United States Patent [19]
Weiss

[11] Patent Number: 5,949,219
[45] Date of Patent: Sep. 7, 1999

[54] OPTICAL STATE-OF-CHARGE MONITOR FOR BATTERIES

[75] Inventor: Jonathan D. Weiss, Albuquerque, N.Mex.

[73] Assignee: The United States of America as represented by the United States Department of Energy, Washington, D.C.

[21] Appl. No.: 09/121,975

[22] Filed: Jul. 24, 1998

[51] Int. Cl.[6] ................................ H02J 7/00; G01N 21/41
[52] U.S. Cl. .................... 320/136; 429/91; 320/DIG. 21; 324/427; 356/135
[58] Field of Search ............................ 320/136, DIG. 21, 320/DIG. 25; 429/90–93; 324/427; 356/135

[56] References Cited

U.S. PATENT DOCUMENTS

| | | | |
|---|---|---|---|
| 3,917,411 | 11/1975 | Schwizer et al. | 356/135 |
| 3,932,038 | 1/1976 | Schweizer et al. | 356/135 |
| 3,977,790 | 8/1976 | Schweizer et al. | 356/135 |
| 4,240,747 | 12/1980 | Harmer | 356/133 |
| 4,329,406 | 5/1982 | Dahl et al. | 429/92 |
| 5,458,992 | 10/1995 | Bailey | 429/93 |
| 5,494,496 | 2/1996 | Huhndorff et al. | 29/623.5 |

*Primary Examiner*—Peter S. Wong
*Assistant Examiner*—K. Shin
*Attorney, Agent, or Firm*—Dickson G. Kehl; James H. Chafin; William R. Moser

[57] ABSTRACT

A method and apparatus for determining the instantaneous state-of-charge of a battery in which change in composition with discharge manifests itself as a change in optical absorption. In a lead-acid battery, the sensor comprises a fiber optic system with an absorption cell or, alternatively, an optical fiber woven into an absorbed-glass-mat battery. In a lithium-ion battery, the sensor comprises fiber optics for introducing light into the anode to monitor absorption when lithium ions are introduced.

37 Claims, 8 Drawing Sheets

OPTICAL STATE-OF-CHARGE MONITOR FOR BATTERIES

The present invention was conceived and developed in the performance of a U.S. Government Contract. The U.S. Government has certain rights in this invention pursuant to contract No. DE-AC04-94AL85000 between the United States Department of Energy and Sandia Corporation.

FIELD OF THE INVENTION

This invention relates generally to an apparatus and method for determining the state-of-charge of a battery in which the change in chemical composition of the conductor with discharge manifests itself as a change in optical absorption.

BACKGROUND OF THE INVENTION

Batteries are devices that convert chemical energy into electrical energy, as a result of chemical reactions between the negative electrode (cathode) and positive electrode (anode) via the intervening electrolyte. Electrode reactions may be described as an electrochemical couple that allows the passage of electrons or ionic species transfer from the anode to the cathode through the intervening electrolyte. The change from electronic conduction to ionic conduction occurs at the electrodes and involves electrochemical or Faradaic reactions. For the purposes of this application, the term conductor is intended to include the entire conducting system of a battery or any component thereof, but particularly the electrolyte and/or the electrodes.

The process of repeatedly or continuously converting chemical to electrical energy causes the battery to discharge, or deplete its capacity for producing electrical energy. Batteries can be classified as either primary or secondary. Primary batteries are assembled with high energy compounds such that the stored chemical energy can be withdrawn as electrical energy at some later time; primary batteries can be discarded without recharge. Secondary batteries are batteries developed to have a recharging capability. Materials used in secondary or storage batteries must be capable of maintaining electrode or electrolyte integrity over repeated charging and discharging cycles.

There are different classes of primary and secondary batteries, and a wide range of choices as to compatible pairs of anode and cathode processes for both primary and secondary batteries. Electrolytes may include, for example, aqueous salt solutions, non-aqueous electrolytes comprising either molten salts, organic or inorganic solvents rendered conductive by dissolved salts, or solid electrolytes. Again, by way of example, for primary batteries such as zinc manganese-dioxide, zinc-zinc chloride-manganese dioxide, zinc alkaline-manganese dioxide, zinc mercuric-oxide, zinc silver-oxide, or magnesium-manganese dioxide, the electrolyte solution is an aqueous solution of ammonium chloride (or zinc chloride), potassium hydroxide, sodium hydroxide, or magnesium perchlorate. For secondary batteries such as nickel cadmium, nickel-iron, nickel-zinc, silver-zinc, silver-cadmium, silver-iron, mercuric oxide-cadmium, or lead-acid, the electrolyte solution can be either potassium hydroxide or sulfuric acid.

Battery depletion may occur through use. More specifically, in today's conventional internal combustion vehicles, battery depletion typically occurs from electrical systems which include loads from clocks, radios, vehicle theft deterrent systems, engine system controls, and others. These loads draw current from a battery when it is not in use, and if sustained over a long period of time, these electrical components may deplete the battery's reserve capacity and render it completely discharged and unusable.

There is an increasing demand for more efficient primary and secondary batteries that will withstand heavy loads. Correspondingly, there is a need for a battery monitoring method that is capable of determining the state-of-charge instantaneously. The state-of-charge of a battery is the amount of available charge (amp hours) the battery can still usefully provide. Accurate monitoring of a battery prevents complete discharge, undercharging and overcharging of the battery, all of which are conditions that damage and/or limit the life of the battery.

There is a further need for a state-of-charge battery monitor to provide an accurate and instantaneous reading regarding the capacity of the battery to the user/operator of the system containing the battery. The user/operator must know the state-of-charge of a battery at all times because, as one example, if the battery's charge is depleted without sufficient warning, the operator of an electric vehicle may be stranded and unable to locate or reach a power source to recharge the battery. Therefore, there is a need for a metering system that reliably provides operators with an accurate and instantaneous indication of the measure of charge left in the battery, and consequently, an indication of the time remaining before recharging the battery is necessary.

More specifically, the current need for electric-powered systems or electric hybrid vehicles have renewed development interest in producing a lead-acid battery (a type of secondary, rechargeable battery) that is both efficient and easy to maintain. Lead-acid batteries, due to widespread availability and use in automotive, industrial, and consumer applications, are particularly desirable for electric-powered systems. The lead-acid battery has an efficient electrochemical system that is highly reversible and can be discharged and charged repeatedly before failure. Therefore, there is a particular need for a metering system that allows for continuous state-of-charge monitoring and that is electrically noninterfering, in the sense that the metering system does not draw or produce current from the battery and will not disturb other circuits in the electric or hybrid vehicle.

The problem of measuring the state-of-charge of primary and secondary batteries is not new. Known primary and secondary battery monitors have been directed to: (1) detecting the specific gravity of the battery electrolyte, (2) measuring the terminal voltages of the battery, and (3) tracking and monitoring the charge drawn from and supplied to the battery.

However, known systems for measuring the state-of-charge of a battery have been unsatisfactory in many areas. At best, these existing methods only yield approximate values for the state-of-charge because they have been designed to monitor and determine the total time of use, or rate of charge transfer of remaining battery capacity, without taking into account one or more of the following factors: ripple current, battery temperature, specific gravity of the electrolyte, and voltage potential across the battery cell terminals in an open circuit, etc. In addition, because these monitors typically monitor the state-of-charge from an electrical perspective, relying on the integration of the current in the battery, these monitors are often susceptible to interferences, and the readings obtained are not instantaneous. Thus, errors can accumulate, and the state-of-charge reading is not entirely accurate. In any case, no known battery monitor has employed optical technologies to determine the state-of-charge of a battery.

U.S. Pat. No. 5,321,389, issued Jun. 14, 1994 to Meister, discloses a battery charge monitor comprising an electronic circuit for connection to a vehicle battery. The circuit is responsive to a battery voltage to provide an electrical signal indicating a voltage drop across the terminals and uses relay coils to open and close the relay contacts for connecting and disconnecting the battery from the loads based on signals.

U.S. Pat. No. 5,321,626, issued Jun. 14, 1994 to Palladino, discloses an apparatus for monitoring and forecasting battery performance using a plurality of probe assemblies that sense output voltages and current across a series of connected batteries. The probe assemblies include a digital output device to display physical parameter information such as electrolyte specific gravity, temperature, individual battery voltage and electrolyte level, for comparison to corresponding fixed physical parameter values.

U.S. Pat. No. 5,339,017, issued Aug., 16, 1994 to Yang, discloses an arrangement of diodes and thyristors for detecting the state-of-charge of a vehicle battery. The individual diodes are arranged to define a predetermined forward voltage drop, which energizes the respective thyristors which energize respective light-emitting diodes (LEDs) to form a bar graph display of the state-of-charge of the battery. The greater the voltage drop across the various electrical loads, the greater the number of diodes which conduct and the greater the number of LEDs which are illuminated.

U.S. Pat. No. 5,345,163, issued Sep. 6, 1994 to Gibbons et al., describes a method for continuously monitoring battery charge level in three monitoring stages: in the first stage, overcharging is prevented if the monitored voltage exceeds a first predetermined voltage, as indicated by a "DO NOT CHARGE" signal; in the second stage, the "OK TO CHARGE" signal appears if the monitored voltage falls below a first predetermined voltage longer than a first predetermined period; in the third stage, the "OK TO CHARGE" signal is maintained until the monitored voltage falls below a second predetermined voltage for a period longer than a second predetermined period, resulting in the "MUST CHARGE" signal.

U.S. Pat. No. 5,381,096, issued Jan. 10, 1995 to Hirzel, discloses a metering system that monitors and communicates the state-of-charge of a battery-powered device to its operator. The apparatus measures the actual terminal voltage of the battery, and a digital electronic model computes the battery's charge by tracking an internal voltage which corresponds to the open circuit voltage of the battery. This internal voltage represents the battery's state-of-charge, and remaining battery life is shown on a visual display.

U.S. Pat. No. 5,483,165, issued Jan. 9, 1996, to Cameron et al. discloses a sense cell for determining remaining capacity and depletion condition of the main battery, based on the concept that by using a battery analogous to the main battery pack as the sense cell, the cell (being exposed to the same environmental conditions) will draw a larger load than that experienced by the main battery pack. Because the sense cell is identical to the cells in the main battery, the degradation of the sense cell and main battery cells is anticipated to be identical. Once the sense cell is fully depleted, a circuit prevents further current from being drawn from the main cells, and the operator is informed that recharging is necessary.

U.S. Pat. No. 5,656,919, issued Aug. 12, 1997 to Proctor et al., discloses a state-of-charge monitoring system for a battery under varying load and temperature conditions as the battery is being charged or discharged. Memory devices store discharge and charge values, and a processor determines the battery's state-of-charge. The Peukert equation is used to determine the battery's state-of-charge based on the battery's depletion condition.

U.S. Pat. No. 5,672,973, issued Sep. 30, 1997 to Arai et al., discloses an apparatus for monitoring the residual capacity of a battery by sensing the discharge current and terminal voltage based on a linear relationship between the terminal voltage and the current during discharge. The residual battery capacity is calculated by averaging the changes in the discharge current and the terminal voltage on a first time scale and obtaining linear functions based on the respective averages.

Other battery state-of-charge tracking devices and monitors are disclosed in the following references: U.S. Pat. No. 5,496,658 to Hein; U.S. Pat. No. 5,619,417 to Kendall; U.S. Pat. No. 5,281,955 to Reich; U.S. Pat. No. 5,047,961 to Simonsen; U.S. Pat. No. 4,949,046 to Seyfang; U.S. Pat. No. 4,947,123 to Minezawa; U.S. Pat. No. 5,633,592 to Lang; U.S. Pat. No. 4,931,738 to MacIntyre; U.S. Pat. No. 5,614,804 to Kayano; U.S. Pat No. 5,596,260 to Moravec; U.S. Pat. No. 5,352,982 to Nakazawa. Again, none of these use optical methods to determine the state-of-charge of a battery.

It is known to detect state-of-charge optically by measuring the changes in the refractive index of a solution (G. P. Hanckc, "A Fibre-Optic Sensor for Monitoring the State-of-Charge of a Lead Acid Battery," *Proceedings of the IEEE Instrumentation and Measurement Technology Conference*, Washington D.C., Apr. 25–27, 1989, pp. 496–489). Hancke describes a fiber-optic technique for determining the specific gravity of a lead-acid battery by monitoring leakage of light through the walls of a fiber contacting the electrolyte, converting the leakage to a related specific gravity value, and thereby determining the state-of-charge of a lead-acid battery. However, Hancke does not describe the use of optical absorption to measure battery charge.

Additionally, currently pending U.S. patent application, Ser. No. 08/566,340, discloses a fiber-optic refractive index monitor that detects small changes in the index of refraction of a liquid with an optical waveguide. The waveguide measures the change in light through a liquid-clad optical fiber having a liquid core, as an indication of state-of-charge of a lead-acid battery. Again, optical absorption is not used to measure battery charge.

Accordingly, there remains an unsolved need for a monitor capable of determining the actual state-of-charge of a battery and communicating that information to the user of the battery-powered system that is functionally useful with a wide range of battery types.

SUMMARY OF THE INVENTION

In view of the above-described needs and to overcome the shortcomings of existing state-of-charge battery monitors, it is an object of this invention to provide a monitor for the state-of-charge of a battery that overcomes the above-noted disadvantages of known battery monitors and that meets the current needs for providing instantaneous and continuous information about the capacity of a battery in use to the operator/user of the battery-powered device.

It is another object of the present invention to provide an optical apparatus and method for measuring the state-of-charge of any battery in which change in composition with discharge manifests itself as a change in optical absorption.

It is a further object of the present invention to provide an optical absorption sensor for use as a state-of-charge monitor that is electrically non-interfering and not susceptible to electromagnetic interference.

It is still another object of the present invention to provide an optical absorption sensor that can continuously monitor and provide the state-of-charge of the battery in real-time under repeated charge and discharge cycles.

It is still further an object of the invention to provide an optical absorption sensor that provides an accurate determination of the battery's state-of-charge without being susceptible to temperature changes or current being discharged from the battery.

To achieve the foregoing and other objects, and in accordance with the purpose of the present invention, as embodied and broadly described herein, the limitations associated with existing battery monitors are overcome by the present invention which provides a simple and efficient apparatus and method for analyzing the charge condition of a battery having an optically interrogatable conductor (electrolyte or electrode). Optically interrogatable in this context is defined as a conductor through which light can be transmitted to obtain spectral absorption information relating to chemical changes that occur in the conductor during the electrochemical reaction that produces the battery's electrical energy, that information being used to derive the optimum wavelengths needed to monitor the overall state-of-charge of the battery in use. Spectral absorption information is the absorption coefficient (absorptivity) of the conductor versus wavelength of the light, relative to the conducting medium through which the light passes.

More specifically, this invention is an optical absorption sensor, comprising a fiber optic system that examines the optical absorption characteristics of the conductor of a particular battery within a chosen optical path, particularly certain chosen absorption peaks or valleys detected in the conductor as light is transmitted through the conductor at the chosen wavelength(s). By plotting these absorption characteristics, using the absorption coefficient of that conductor versus wavelength to obtain the absorption spectrum wavelength for that conductor as a function of state-of-charge of the battery, the operating wavelength of the sensor is pre-chosen for the type of battery and conductor to be monitored.

In use, absorption in the battery's conductor changes during operation of the battery as it discharges, and the change is detected by the inventive sensor as changes in received optical power corresponding to the change in absorption (e.g., the lowering of a peak or the heightening of a valley). Conventional equipment, e.g., light source, photodetector, trans-impedance amplifier, microprocessor, is used to provide light to the sensor and to transmit the collected information, in a meaningful format, from the sensor of the invention to the user of the device containing the battery.

In one embodiment, the optical sensor comprises a housing and a plurality of optical fibers, preferably a bundle comprising six receiving fibers surrounding a central transmitting fiber. The housing, which is inserted into the conductor (electrolyte), contains at least two openings to allow the liquid electrolyte to fill it, and an interior reflecting surface shaped to provide the maximum return signal, i.e., flat, concave, convex, curved or curved in some other fashion. One end of the fiber optic bundle comprises a polished face that is sealed to the housing, thus forming part of one wall of the housing. The central transmitting fiber of the bundle is operably connected to a light source, while the six receiving fibers are operably connected, as a bundle, to a photodetector.

In using this embodiment, light is emitted from the light source, emerges from the central transmitting fiber, is transmitted through the electrolyte, reflects off the reflecting surface, and returns to the six receiving fibers. The reflected light returned to the receiving fibers is changed in optical power corresponding to changes in absorption in the conductor during discharge of the battery. Typically, the light source and the photodetector are remotely located. This implementation is compatible with the geometry of a lead-acid battery, where the sensor measures the decline in the optical attenuation at certain characteristic absorption peaks of pure water.

In another embodiment of the present invention, the conductor (which is an electrolyte in this case) serves as the lossy cladding of an otherwise unclad optical fiber. This implementation is compatible with the geometry of an absorbed glass-mat battery where the sensor optical fiber is woven into the mat. More specifically, the electrolyte is absorbed into the glass mat which acts as a sponge, and an unclad optical fiber is woven in with the other structural fibers to allow determination of the state-of-charge of the battery.

The optical absorption sensor of the present invention is useful with a variety of battery types. For example, in use with a lithium-ion battery, the sensor measures optical absorption in the conductor (anode, e.g., cobalt oxide, manganese oxide, etc.) as lithium ions are added to it during discharge of the battery, thus generating absorption peaks within one or more appropriate wavelength bands.

Advantageously, by focusing on changes to the optical properties of the battery as detected by looking at the absorption in the conductor as light is transmitted through it, the optical absorption sensor of the present invention eliminates the need to measure conventional physical parameters such as discharge time, main battery voltage, or resistance to determine a battery's state-of-charge.

Additional objects, advantages and novel features, and further scope of applicability of the present invention will be set forth in part in the detailed description to follow, taken in conjunction with the accompanying figures, and in part will become apparent to those skilled in the art upon examination of the following detailed description, or may be learned by practice of the invention. The objects and advantages of the invention may realized and attained by means of the instrumentalities and combinations particularly pointed out in the appended claims.

BRIEF DESCRIPTION OF THE DRAWINGS

The accompanying drawings, which are incorporated in and form part of the specification, illustrate an embodiment of the present invention and, together with the description, serve to explain the operation, features, and advantages of the invention.

DETAILED DESCRIPTION OF THE INVENTION

Figure 1:
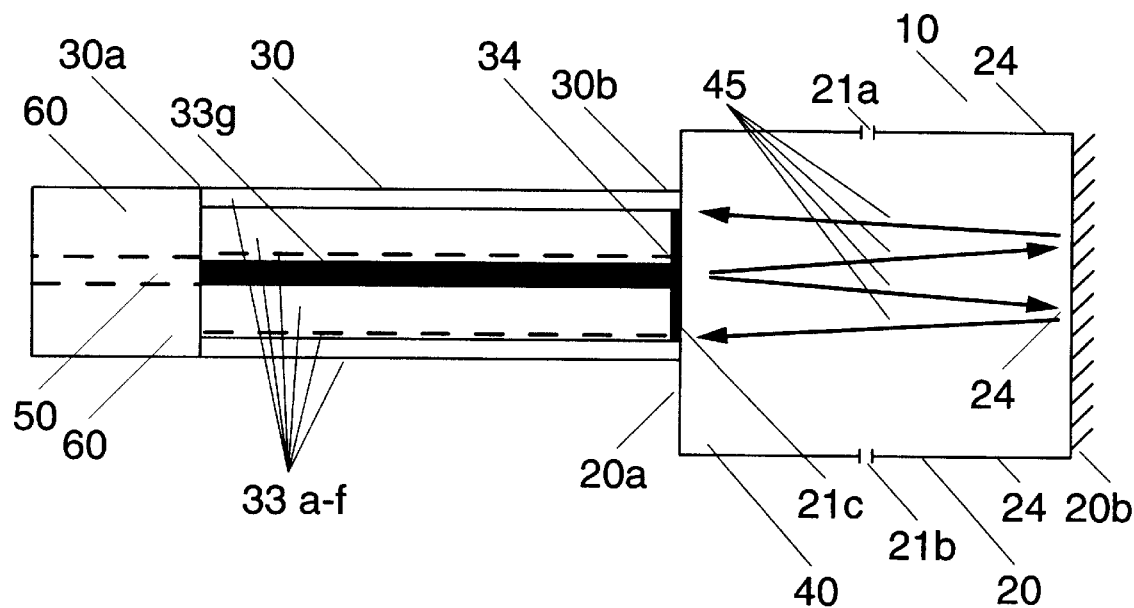
FIG. 1 is a schematic of one embodiment of the optical absorption sensor of the invention.

The present invention comprises an apparatus and method for determining the state-of-charge of a battery in which the change in chemical composition inherent in the discharge of the battery as electrical energy is produced from chemical energy, manifests itself as a change in optical absorption and ultimately a change in optical power in light passing through the conductor of the particular battery. The optical absorption sensor of the present invention is designed for use with any primary or secondary battery where the battery's conductor (defined herein to be either electrolyte or electrode) is optically interrogatable, that is, where the conductor can be contacted with light to obtain information relating to the above-described chemical changes that occur in the conductor during the electrochemical reaction that produces the battery's electrical energy, that information being used to derive the optimum wavelengths needed to monitor the overall state-of-charge of the battery in use.

Information obtained from the passage of light through the conductor is defined as spectral absorption information, i.e., the absorption coefficient (absorptivity) versus wavelength, relative to the conducting medium through which the light passes. The term absorbance as used here may be defined as a multiplicative constant (1/2.3) multiplied by the product of the absorption coefficient and the thickness of the medium through which the light is passing, i.e., the pathlength. Absorption is the process by which light is lost (absorbed, scattered) in the conductor of a battery and is monitored by the inventive sensor in connection with a specific battery. Absorption scales with absorbance, i.e., the larger the absorbance, the larger the absorption. The amount of light lost (absorption) in the conductor depends exponentially on absorbance. The inventive sensor may be used with any battery that is optically interrogatable along an optical path chosen for a desired range of wavelengths, where the absorption occurs within a chosen spectral band (as an example only, usually a band within the near ultraviolet to near infrared). In a practical sense, in the sensor of the invention, optical absorption in the conductor is manifested as a change in optical power emerging from the conductor.

The inventive sensor comprises a fiber optic system that examines the optical absorption characteristics of a known conductor of a particular battery within a chosen optical path, more particularly changes detected in the conductor with discharge of the battery, the changes being those occurring in a chosen region of the conductor's absorption spectrum as light passes through it. Absorption in the conductor changes during operation of the battery as it discharges, and the change is detected by the inventive sensor. Specifically, the fiber optics detect changes in optical power occurring in the conductor during discharge of the battery by transmitting light through the conductor at a predetermined wavelength, the changes in optical power representing changing absorption in the conductor, and convert the changes in optical power to information about the battery's state-of-charge, that information being communicable to the user of the battery in real-time.

The optimum wavelength for the sensor is a function of the particular conductor and its behavior during discharge of the battery and is predetermined by obtaining spectral absorption information at a chosen limit of its chemical composition (e.g., absorption peaks) occurring in the conductor (electrolyte or electrode) during the passage of light. Light is transmitted through the conductor at several wavelength(s). One or more operating wavelengths are pre-chosen for the sensor depending on the type of battery and conductor to be monitored, using a plot of absorption coefficient versus wavelength to obtain the absorption at that wavelength for that conductor as a function of state-of-charge of the battery.

Communication of the information collected by the sensor of the invention, in a meaningful format, to the user of the device containing the battery, is accomplished by means of a photodetector which receives the light transmitted through the conductor and converts it to an electric current proportional to the optical power falling on the detector, a means of converting that current to a voltage (e.g., a transimpedance amplifier) proportional to the electric current produced by the detector, a microprocessor to convert the voltage signal from the amplifier to a state-of-charge, and a means for displaying the resulting information. The display means communicates the state-of-charge information to the user of the device having the battery by some conventional means (e.g., a gauge). In the absence of a direct proportionality between the optical power falling on the detector and the state-of charge (i.e., if the electrical signal from the changing light transmission is not exactly proportional to the state-of-charge), a mathematical calculation may be made by the microprocessor to complete the conversion of the voltage signal to another signal that is proportional to the state-of-charge.

The physical parameters associated with both the structure and the operation of the optical absorption sensor are not fixed, but are determined by the type and construction of the battery and the chemical composition and transparency of the conductor (electrolyte or electrode). Also, in use, the optical absorption sensor of the present invention may be located internal or external to the battery, depending on the size of the battery, the space requirements, and the optical transparency of the battery casing. The controlling consideration for these choices is the strength of the signal needed for a successful operation. These parameters are chosen to produce the optimum dynamic range of the sensor, or the most detectable signal.

Specifically, the wavelength and the pathlength used for the optical absorption sensor are predetermined to conform to the chemical and optical characteristics of the battery's conductor. An appropriate wavelength or spectral band is one at which absorption is a strong function of the changes in chemical composition that occur during discharge of the battery. When several such spectral bands exist, as in the case of a lead-acid battery, additional considerations, such as the availability of optical sources, the responsivity of optical detectors, and the transmission of optical fibers will determine the choice. The pathlength also is pre-chosen to produce a reasonable range of signals under the same circumstances, e.g., too short a pathlength produces little absorption at any state-of-charge, and too long a pathlength produces excessive absorption at any state-of-charge. As an example of these considerations, the more transparent the electrolyte of the battery, the longer the operable pathlength. Also, in embodiments associated with lead-acid batteries, the chosen pathlength may dictate the length of the sensor housing or the absorption cell.

The light source to be used with the invention may be any of several sources, examples being a laser diode, light-emitting diode, an incandescent bulb appropriately filtered for the wavelength range of interest, or any other source of light that is geometrically compatible with the fiber optic system and that emits at an appropriate wavelength. The method of interrogation typically comprises one or more optical fibers. Examples include one fiber where multiple reflections occur at the interface between the fiber and the conductor, or an absorption cell containing a reflector (reflecting surface) and used with an optical waveguide, where the waveguide pipes light into the cell, receives the reflected light returned from the cell, and sends the reflected light to the detector. The particular optical fibers are chosen to transmit the light at the chosen wavelength as fully as possible, i.e. they are as transparent as possible for that wavelength. The detector is also chosen to be responsive at the chosen wavelength, examples being a photodetector, such as a silicon detector, an indium antimony detector or an indium gallium arsenide detector. All of the various structural elements connected to the operation of the sensor, e.g., photodetector, resistor, microprocessor, trans-impedance amplifier, and display means, may be conventional, the specific choices of equipment being governed by the considerations discussed above, as well as any other practical considerations, such as the need to minimize the draw of current from the battery.

The optical absorption sensor of the invention is particularly applicable to lead-acid batteries; the inventive sensor provides an accurate and efficient means of indicating the instantaneous state-of-charge of a lead-acid battery, in both flooded or absorbed glass-mat configurations. In use with a lead-acid battery, the optical absorption sensor takes advantage of the physical phenomena that the sulfuric acid electrolyte has a certain definite absorptivity as a function of its specific gravity (or its acid concentration), and this principle is used to determine the battery's state-of-charge. The electrically induced changes in sulfuric acid to water reduce the optical absorption at certain absorption peaks of pure water with an accompanying drop in the concentration of water molecules. The sensor determines in real-time the specific gravity or acid concentration of the electrolyte by measuring changes in optical absorption of the electrolyte at wavelengths of certain optical absorption peaks of pure water. The height of these peaks will diminish with increasing sulfuric acid concentration. Depending on the concentration of sulfuric acid in the lead-acid battery, the sensor provides to the photodetector a signal changing in optical power which represents data relating to the absorption at the chosen wavelength of the peaks of pure water in a diminishing sulfuric acid condition (typical of discharge of a lead-acid battery). Alternatively, the sensor could be programmed to respond to absorption peaks associated with the changing sulfate ion concentration in the conductor. In this case, the optical transmission increases as the battery discharges.

In using the inventive sensor with the lead-acid battery, the higher the absorbance determined from the data obtained, the more the power of the battery has diminished; in other words, the transmitted optical power incident (falling) on the detector diminishes as the battery discharges. Whether monitoring the diminishing sulfuric acid condition or the increasing sulfate ion condition, the data obtained by the detector is then used to calculate the state-of-charge of a battery in real-time, the calculation being performed by a programmed computer processor, and the program being designed to convert electrical light signals received from the photodetector to readings indicative of the battery's state-of-charge.

The optical absorption sensor of the present invention is also effective for batteries where the electrolyte negligibly changes upon discharge, such the lithium-ion battery where lithium is added to the anode during discharge. In a lithium ion battery, the addition of lithium is analogous to the addition of sulfate ions in a lead-acid battery, except that where, in the lead-acid battery, absorption diminishes as the sulfate ions diminish with use of the battery, in the lithium ion battery, absorption increases with an increase in lithium ions during use of the battery.

In operation, lithium ions leave the negative electrode and enter the positive electrode, and the optical sensor of the invention "interrogates" the electrode, more specifically the anode. The optical absorption sensor of the present invention introduces light into the anode and monitors the state-of-charge of the lithium-ion battery by monitoring the absorption in the anode when lithium ions are introduced; again at a pre-chosen wavelength and within a reasonable optical path, i.e., a range where not all the light is absorbed, and not all the light is transmitted, by the electrode. In use with the lithium-ion battery, the sensor may comprise a waveguide/absorption cell structure as described for use with a lead-acid battery, except that, again, the optical waveguide interrogates the electrode (anode) of a lithium-ion battery, which is typically a solid, instead of the electrolyte as in the lead-acid battery.

FIG. 1 is a schematic of an embodiment of the optical absorption sensor of the invention illustrating the absorptive state-of-charge sensor as it may be used with, for example, a lead-acid battery. As shown in FIG. 1, optical absorption sensor 10 comprises housing 20, having opposite ends 20a and 20b, and an optical waveguide 30, having opposite ends 30a and 30b, for piping light into housing 20. Housing 20, which is inserted into the electrolyte 40 of the battery, contains two openings 21a and 21b to allow the liquid electrolyte 40 to fill it and to flow through it. The length of the housing 20 is chosen to be essentially half the pathlength of the light to be transmitted and to produce the desired range of absorption throughout discharge. For example, a housing that is too short will absorb very little light, regardless of sulfuric acid concentration; one that is too long will absorb essentially all of it under the same conditions.

Housing 20 further includes an interior reflecting surface 24 comprised of the internal housing wall 24 at end 20b opposite the point of light entry into housing 20. Interior reflecting surface 24 may be flat, convex, concave or curved in any manner that will optimize the peak return signal from the electrolyte 40. In other words, interior reflecting surface 34 is formed in whatever shape will best control the way in which light emerges from, and is received into, housing 20. The multifiber configuration will result in an output that is peaked at a particular separation between the fiber face and the reflecting surface. That separation is a function of the curvature of the reflecting surface, the fiber's numerical aperture, and the packing of the fibers within the bundle. The curvature of the surface is chosen to yield a convenient optical pathlength.

In embodiments using a housing such as that shown in FIG. 1, the reflecting surface 24 is opposite the location where light is emitted into the conductor. In embodiments where there is no housing, the reflecting surface is the structural interface between the fiber optics and the conductor, which reflects the transmitted light.

Optical waveguide 30, as shown in this embodiment, comprises a plurality of optical fibers, preferably a bundle 30. Bundle 30 is shown here as including six receiving fibers 33a–33f surrounding a central transmitting fiber 33g, and being attached at its end 30b to housing 20 at its end 20a .

Central transmitting fiber 33g of bundle 30 is connected to a light source (not shown) by lead fibers 50 at end 30a of bundle 30, while the six receiving fibers 33a–33f are connected to a photodetector (not shown) by lead fibers 60, also at end 30a of bundle 30. Both the light source and the photodetector are remotely located from sensor 10. It is an advantage of the optical absorption sensor of the present invention that, aside from providing geometric flexibility, use of optical fibers allows all light sources and detectors to be remotely located. It should be noted that, in any given use of the inventive sensor, if the fibers 30 are long enough to contact the source and detector, no additional lead fibers 50 and 60 will be necessary.

The end 30b of the fiber optic bundle 30 comprises a polished face 34 that is inserted into a third opening 21c in the housing 20 and is sealed to it; face 34 contributes to the prevention of scattering of the reflected light in various directions. It should be noted that, as an alternative, bundle 30 may be located inside or outside of housing 20. For instance, the third opening 21c may be covered by a window (not shown), with the fibers of the bundle 30 attached either to, or near, the window. Transmitted light would then pass through the window into the absorption cell. Possible advantages of a such a configuration include better resistance to corrosion by the window (as opposed to the fibers) and potentially easier assembly.

In performance, using the optical absorption sensor of this embodiment, central transmitting fiber 33g introduces light from the remote light source into the electrolyte 40, and the six surrounding fibers 33a–33f receive light reflected from interior reflecting surface 24. As shown in FIG. 1, light emerging from the central fiber 33g passes through the electrolyte 40 and reflects off interior reflecting surface 24 at far end 20b of housing 20 and back into the six surrounding receiving fibers 33a–33f, being partially absorbed in the electrolyte. This reflection is depicted in FIG. 1 by ray paths 45. In this manner, in a lead-acid battery or in any other battery system that uses water (an aqueous system) in the electrolyte, the decline in the optical attenuation at certain characteristic absorption peaks of pure water may be measured.

The reflected signal (the return signal) enters the six receiving fibers 33a–33f which guide it to the remotely located photodetector. The photodetector produces an electrical current that is proportional to the optical power incident (falling) on it, which, in the case of the lead-acid battery and when absorption at the peaks of water is being monitored, diminishes as the battery discharges. As an example, however, the opposite is true when absorption connected with sulfate ions is monitored, in which case optical power increases as the battery discharges. For a fixed geometry, the optical power falling on the detector will depend in direct proportion on the total absorption of the transmitted light by the electrolyte 40 and, hence, on the state-of-charge of the battery.

The electrical current produced by the photodetector is converted to a voltage by means of a trans-impedance amplifier (also remotely located and therefore not shown), the output of which serves as the input to a conventional microprocessor (again, not shown), or a similar means of converting the voltage output of the amplifier. The microprocessor calculates a state-of charge of the battery using an algorithm and the input voltage information, and transmits the calculated state-of-charge information to a conventional display means (not shown), which provides information readable by a user as an indication of battery charge via an appropriate indicator, e.g., gauge.

With regard to this specific embodiment, it should be noted that one of the advantages of using a bundle, rather than a single fiber to send and receive the light, is that the optical power entering the six receiving fibers 33a–33f as a function of distance to the reflecting surface peaks at a particular value of this distance. This value depends on the numerical aperture of the optical fibers used and the curvature of the reflecting surface 24, among other things, e.g., refractive index of the medium (conductor) through which the light passes, and the lateral separation among the fibers. Working at the distance that is designed to give the peak signal not only provides the maximum signal, but also insensitivity of the signal to small changes in the distance that may occur for any number of reasons. This distance may be optimized relative to the absorption characteristics of the electrolyte at a particular absorption peak, in order to produce a desired variation in output from a fully charged to a fully discharged battery.

Figure 2:
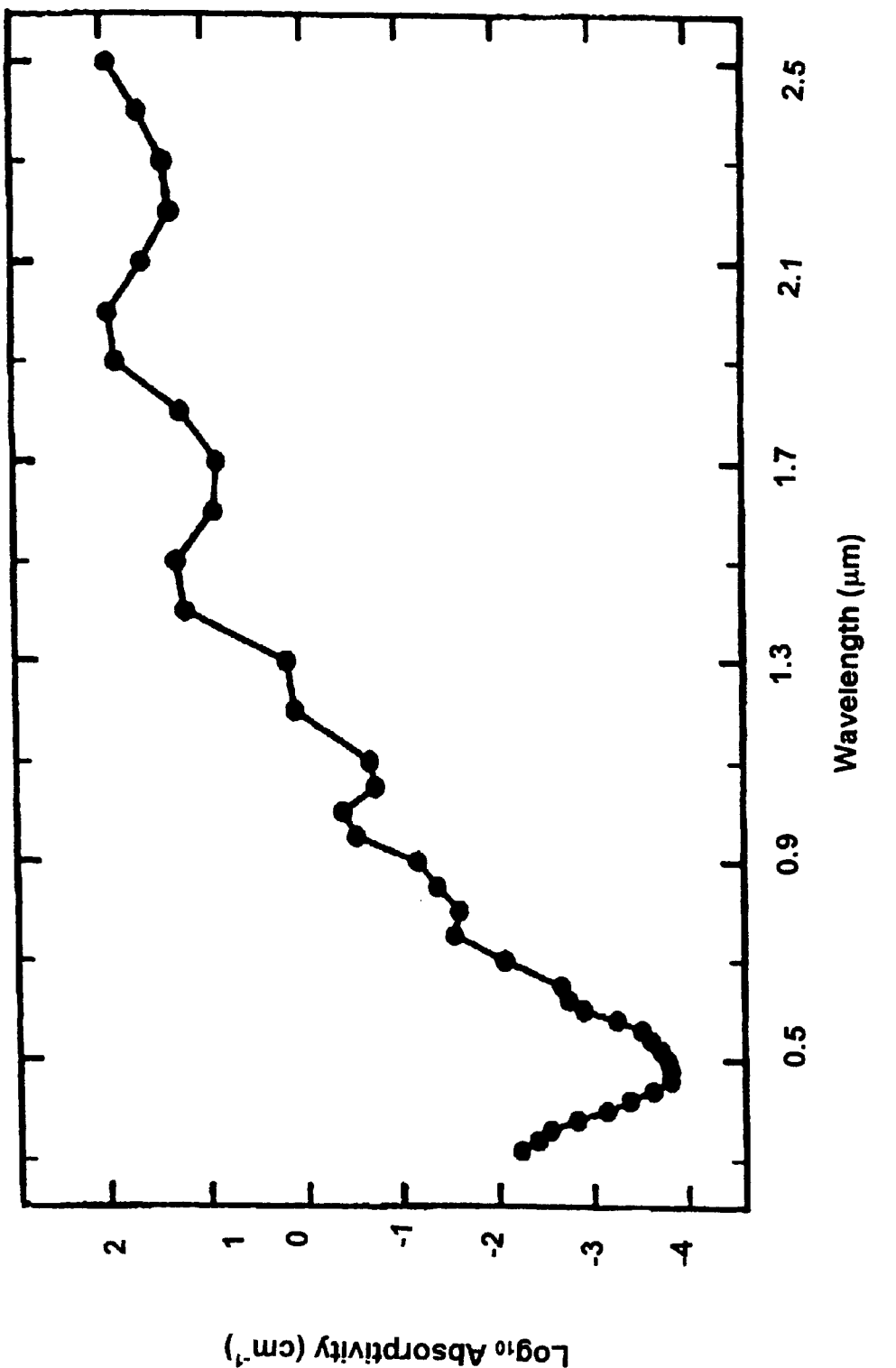
FIG. 2 is a graph of absorptivity vs. wavelength showing the absorption spectrum for pure water.

The concept behind the optical absorption sensor of the present invention can be illustrated further using a lead-acid battery example. The addition of sulfuric acid to water reduces the number of water molecules in the optical path in a lead-acid battery during discharge, and any changes in the concentration of sulfuric acid are accompanied by changes in the optical properties of the electrolyte. FIG. 2 is a graph of absorptivity vs. wavelength showing the known absorption spectrum for pure water, where absorptivity is the absorption coefficient. The temperature used to obtain the data is presumed to be room temperature. As shown in FIG. 2, in the visible and near infrared region, the absorptivity (absorption coefficient) of pure water exhibits various peaks associated with the vibrational states of water in the field of its neighbors. Specifically, the presence of absorption peaks appears at 0.97, 1.2, and 1.45 micrometers, although the absorption peak at 1.2 micrometers is not fully visible because the data are under resolved. It is also known that the specific gravity of the sulfuric acid solution in fully charged battery is nominally 1.3 while in a fully discharged battery, the specific gravity of the sulfuric acid solution is about 1.1.

Figure 3:
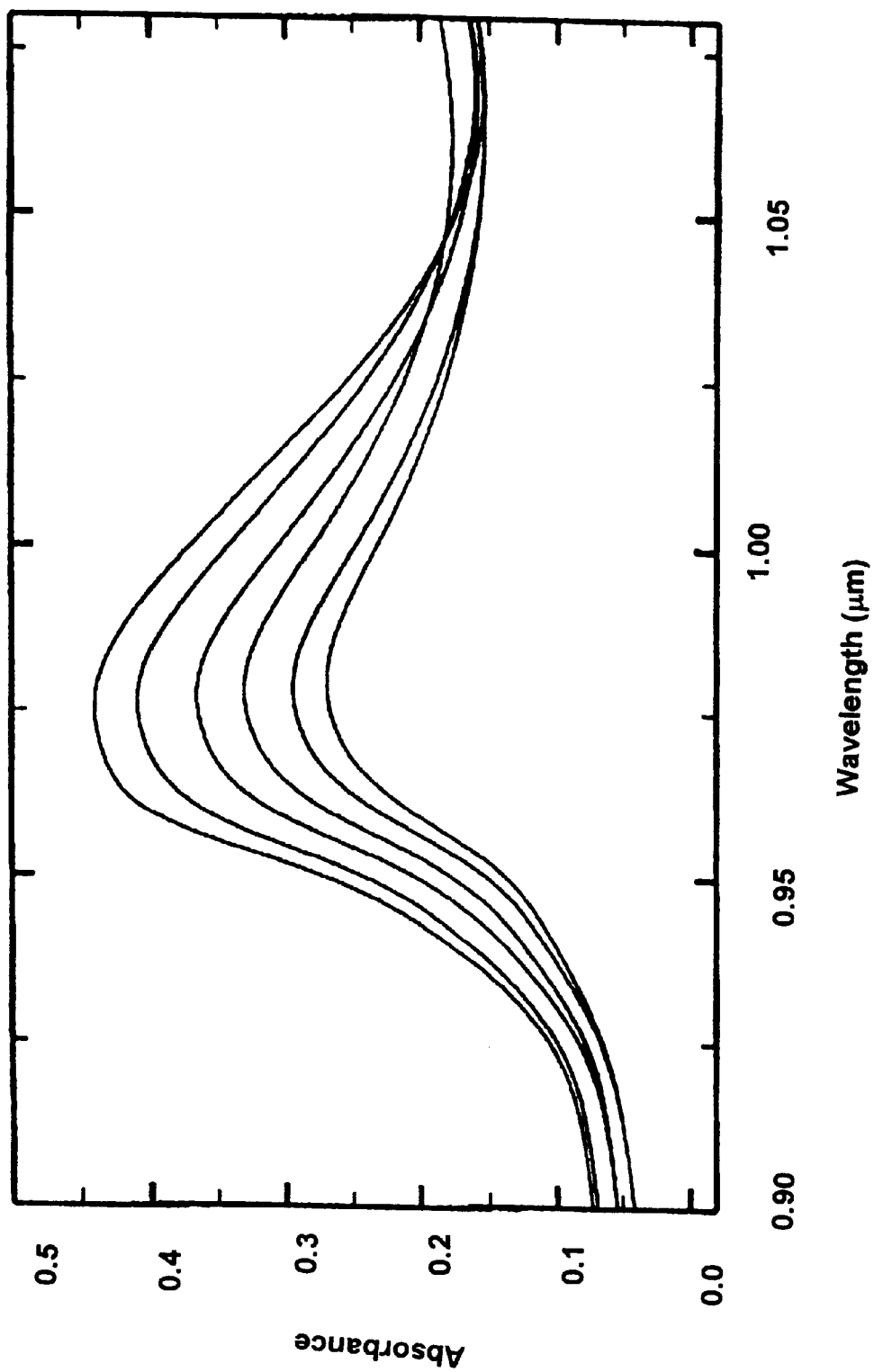
FIG. 3 is a graph of absorbance vs. wavelength for various aqueous solutions of sulfuric acid in the vicinity of 0.97 $\mu$m where the pathlength of the light is 20 mm.
Figure 4:
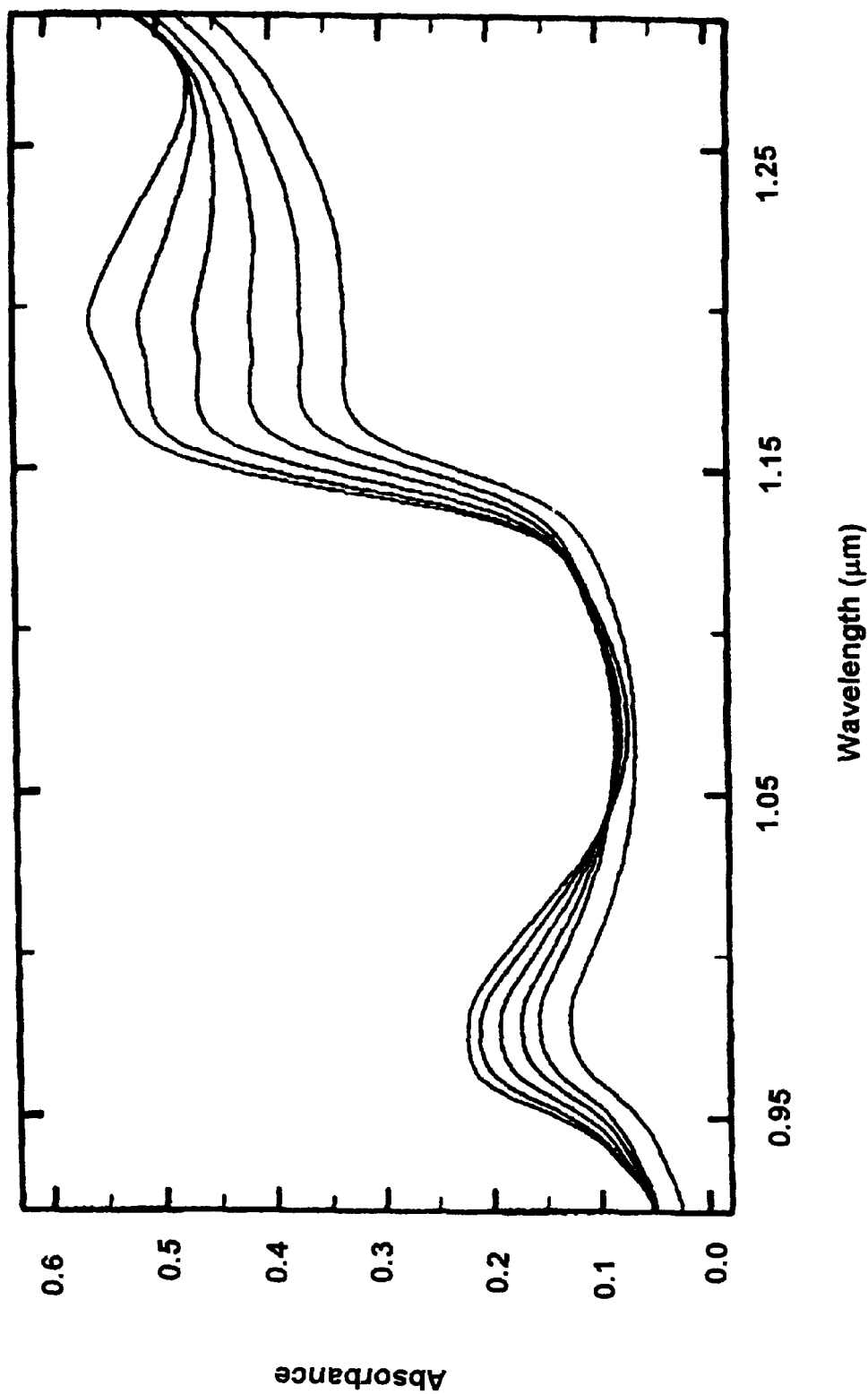
FIG. 4 is a graph of absorbance vs. wavelength for several aqueous solutions of sulfuric acid in the vicinity of 1.20 $\mu$m with a pathlength of 100 mm.
Figure 5:
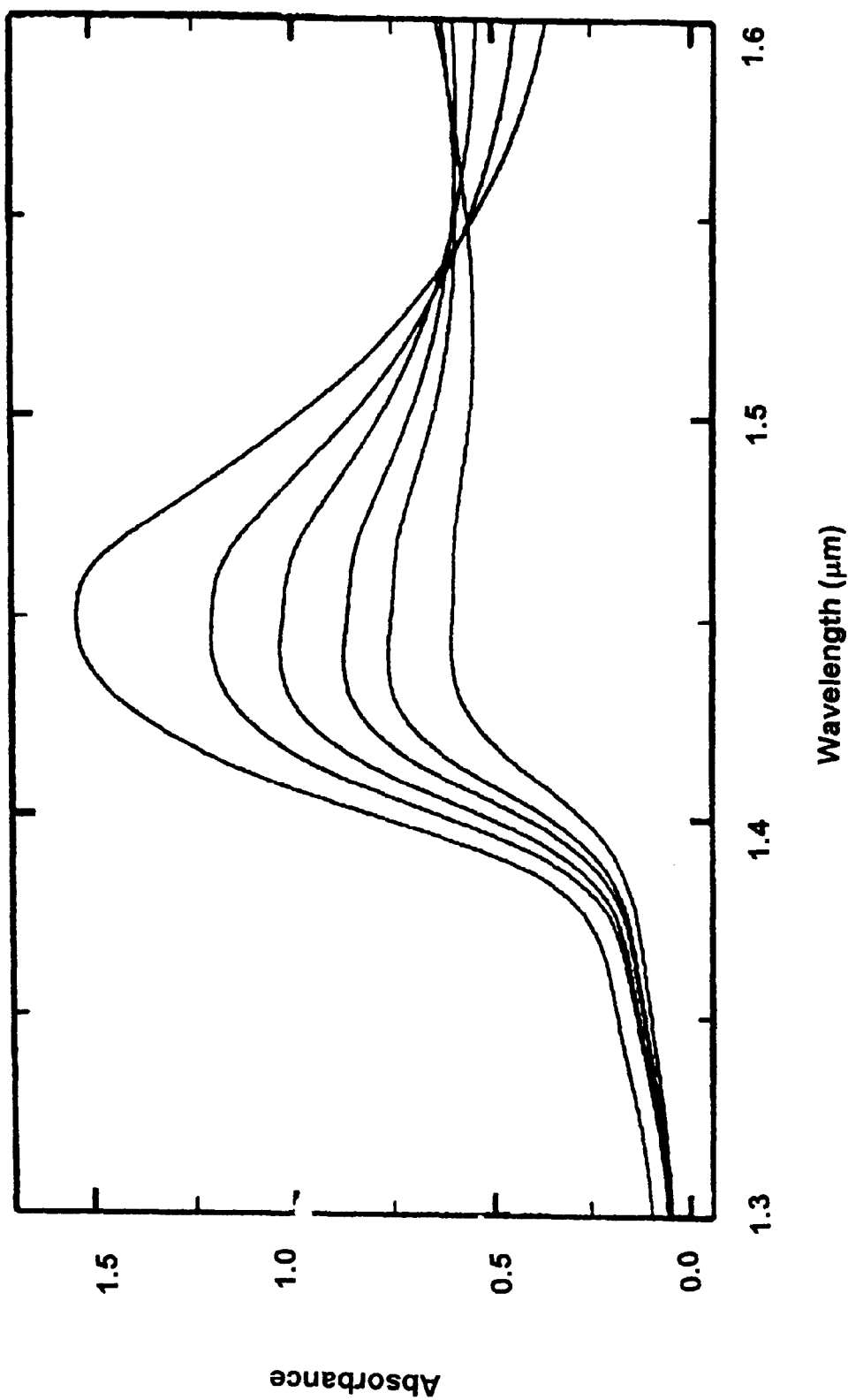
FIG. 5 is a graph of absorbance vs. wavelength for various solutions of sulfuric acid in the vicinity of 1.45 $\mu$m.

Verification studies using the lead-acid battery were performed to validate the optical absorption sensor of the present invention. The optical absorption of aqueous sulfuric acid solutions was studied in the vicinity of water's absorption peaks at 0.97, 1.20, and 1.45 micrometers (chosen because of the data in FIG. 2) in a nominal room-temperature laboratory environment of 23° C. FIGS. 3, 4 and 5 are graphs of absorbance vs. wavelength showing absorbance curves for several aqueous sulfuric acid concentrations in a lead acid-battery. FIG. 3 shows absorbance curves for sulfuric acid solutions in the vicinity of 0.97 $\mu$m where the pathlength of the light is 20 mm. FIG. 4 shows absorbance curves for sulfuric acid solutions in the vicinity of 1.20 $\mu$m with a pathlength of 10 mm. FIG. 5 graphs absorbance curves for various aqueous solutions of sulfuric acid in the vicinity of 1.45 $\mu$m using a pathlength of 1.0 mm. For all three Figures, from the highest to the lowest absorbance, the curves are for solution densities of 1.0, 1.099, 1.303, 1.375, and 1.449 gm/cc. It should be noted that solution density increased with sulfuric acid concentration.

The size of water's absorption coefficients at these wavelengths is such that neither inconveniently large nor inconveniently small optical pathlengths were needed to produce reasonable attenuation. A tungsten bulb was the light source for this work, and the appropriate spectral bands around the absorption peaks were obtained from its broad band emission by a Nicolet 800 Fourier Transform Spectrometer. A silicon detector was used in the 0.97 micrometer region, while an indium antimony detector was used in the other two regions.

Absorbance is defined in this context as $\log_{10}[1/R]$, where R is the ratio of the optical power falling on the detector with the solution in the optical path to that with only air. These measurements cover a density range from 1.0 gm/cc to 1.45 gm/cc, which is wider than that expected from a lead-acid battery. Because the lead-acid battery was the standard used in these determinations, it was observed that the absorbances monotonically diminish with increasing sulfuric acid concentration because there are simply fewer water molecules doing the absorbing at the characteristic wavelength.

It should be noted that the absorption decreases with increasing concentration of sulfuric acid. FIGS. 3,4, and 5 demonstrate that there is a substantial effect on the optical absorption of water with changing sulfuric acid concentration during discharge, the three findings described below verify that the optical absorption characteristics of water are substantially affected by a changing sulfuric acid concentration, as would occur during the discharge of a lead-acid battery.

Figure 6:
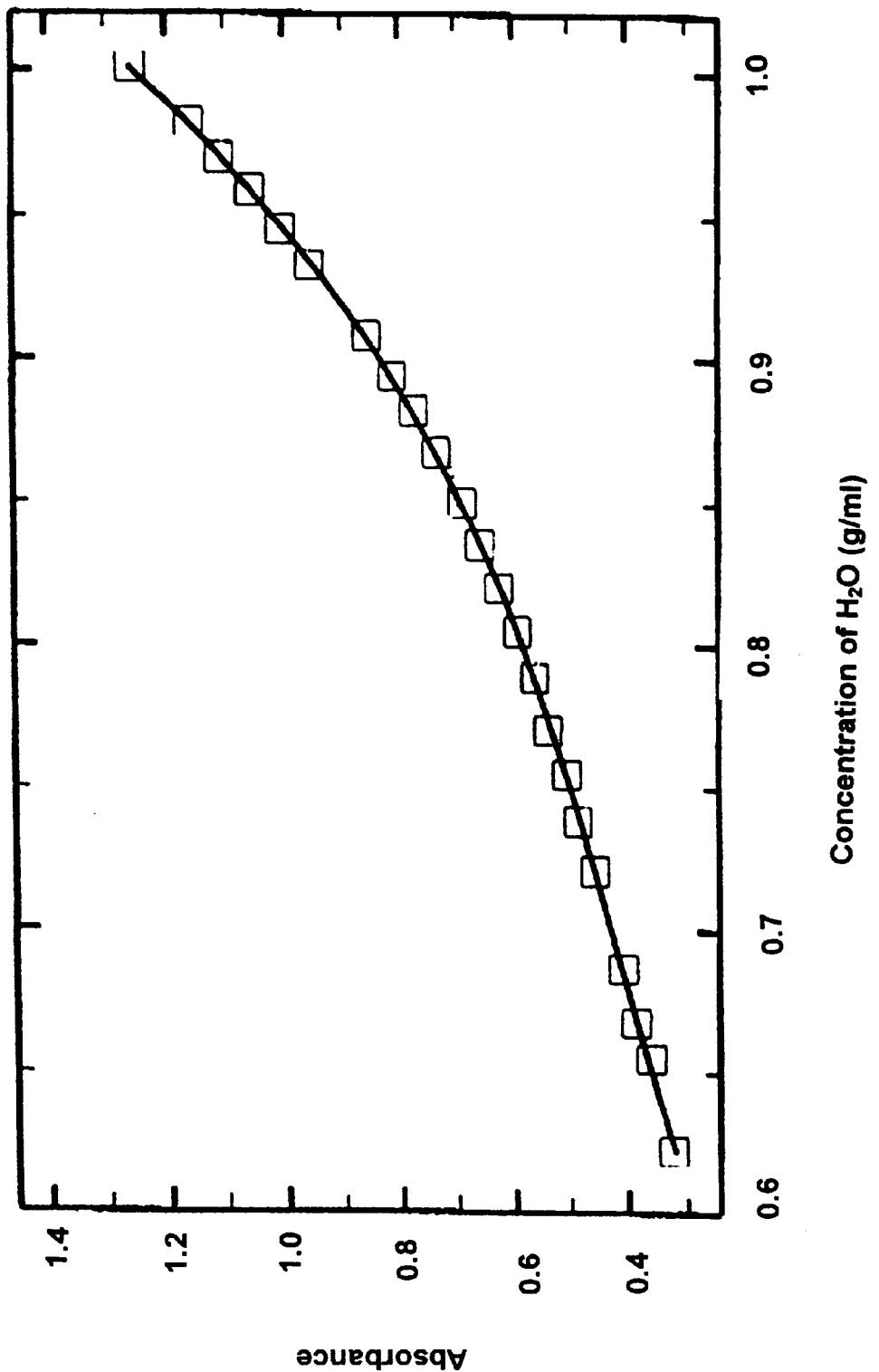
FIG. 6 is a graph of absorbance vs. wavelength showing the baseline-corrected absorbance curve at 1.45 $\mu$m versus water density in various aqueous solutions of sulfuric acid.

FIG. 6 is a graph of baseline-corrected absorbance at 1.45 micrometers versus water density in various concentrations of aqueous sulfuric acid showing a variety of absorption measurements. The baseline was considered to be the general upward trend in absorbance with wavelength. The upward trend to the right of 0.5 micrometers is clear from the data of absorptivity versus wavelength for pure water (FIG. 2). The baseline at a particular absorption peak was obtained by drawing a line connecting the two points on either side of it; however, this baseline was obtained using detailed experimental data rather than the under-resolved data shown in FIG. 2. Thus, for FIG. 6, baseline corrected absorbance is the difference between the absorbance at a particular wavelength within the absorption peak, such as the peak value itself, and the baseline value at that particular wavelength.

In FIG. 6, the solution density corresponding to the lowest water density is about 1.47 gm/ml. As the density of the solution increases, the concentration of sulfuric acid also increases. Thus, the absorbance decreases with increasing sulfuric acid concentration because some of the water molecules in the optical path of pure water are displaced. The graph in FIG. 6 shows a non-linear behavior of the absorbance as it monotonically increases with the molecular density of water. This non-linear behavior illustrates data where a micro-processor-based calculation is needed to derive the state-of-charge from optical absorption.

Figure 7:
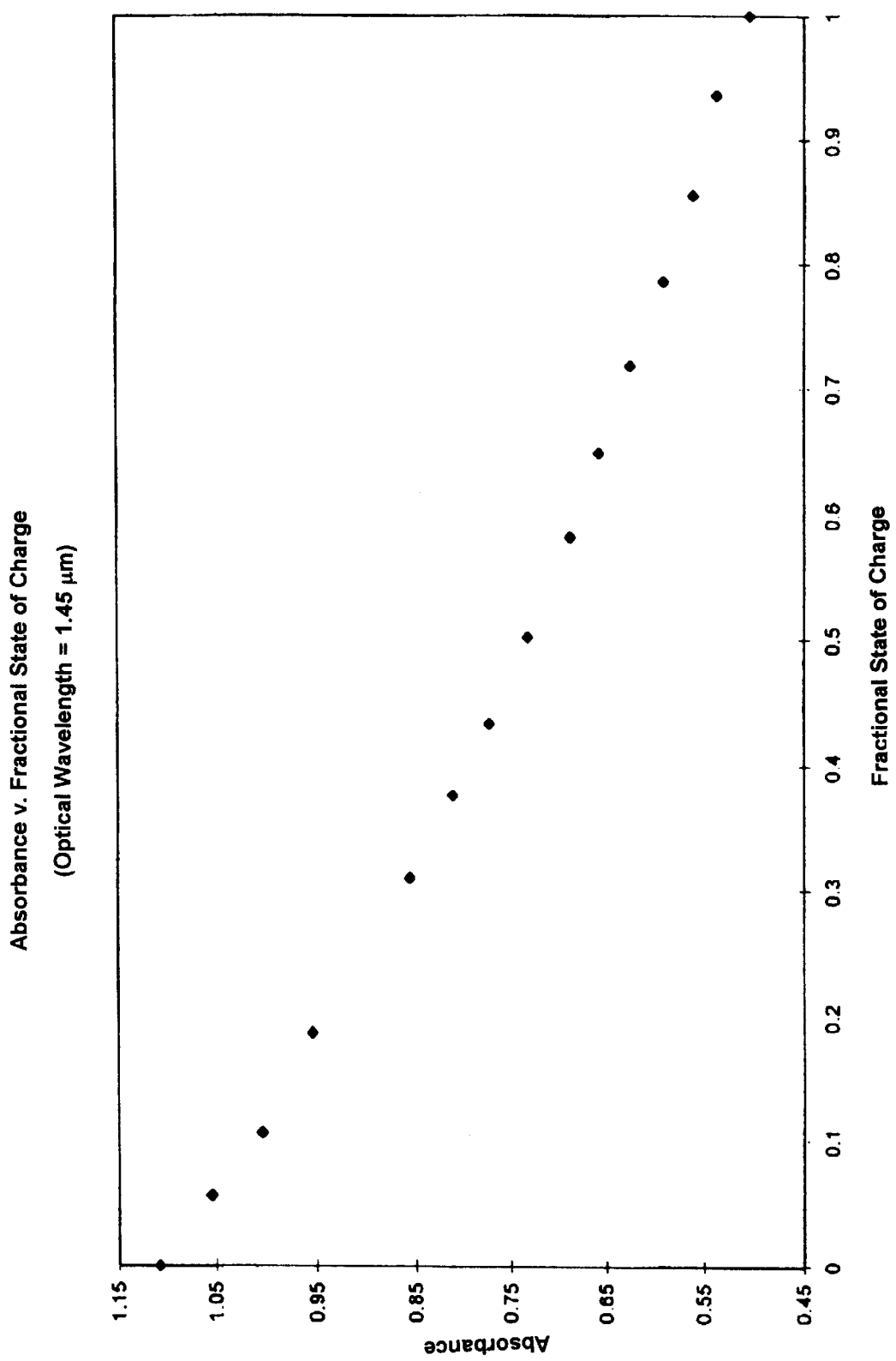
FIG. 7 is a graph of absorbance at 1.45 μm vs. fractional state-of-charge of a lead-acid battery.

FIG. 7 illustrates the relationship of the data collected in these studies to the use of the inventive sensor to monitor a battery's state-of-charge, using again the example of the lead-acid battery. FIG. 7 is a graph of absorbance vs. fractional state-of-charge showing the state-of-charge of a lead-acid battery plotted against the absorbance peak at 1.45 $\mu$m of pure water in sulfuric acid during discharge. The data shown in FIG. 7 is derived from the data shown in FIG. 6. The foregoing physical phenomena (i.e., the phenomena illustrated by FIGS. 4, 5, 6, and 7) makes possible the establishment of a quantitative relationship between the decline in the optical attenuation at certain characteristic absorption peaks of pure water to the concentration of sulfuric acid during discharge.

The fractional state-of-charge is defined as: [SC–SC (at discharge)] /[SC(full charge)–SC(at discharge)], where SC is the state-of-charge of the battery at some point between full charge and discharge. The parenthetical note fixes it at full charge or discharge. Thus, the fractional state-of-charge varies between 0 and 1, states corresponding to "empty" or "full" respectively. In lead-acid batteries, at full charge, the electrolytic solution is about 43% by weight sulfuric acid, and at full discharge, the solution is about 7.5% by weight sulfuric acid. The state-of-charge varies linearly with weight percent between these two extremes.

In another embodiment (not shown), bundle 30 of FIG. 1 is replaced by a single fiber configured with a fiber-optic splitter to separate the transmitted light from the received light. However, in contrast to a single fiber, it is characteristic of the multi-fiber configuration of the present invention that the optical power entering the receiving fibers 33*a*–33*f* does not monotonically diminish with the distance between the fibers and the reflecting surface 24. In performing a sensing operation using the multi-fiber embodiment shown in FIG. 1, the power initially rises with distance, reaches a peak, and then diminishes; using the single fiber with splitter embodiment, the power just diminishes. Because the position of the peak is determined by lateral separation between the fibers, their numerical aperture, and the curvature of the reflecting surface, there is an advantage of working at the fiber-reflector separation corresponding to the peak in the multi-fiber configuration of FIG. 1, in that the return signal is insensitive to small changes in this separation. This insensitivity minimizes a potential source of error in the overall measurement. Therefore, because such a peak does not exist when using the single fiber/fiber-optic splitter configuration, some mathematical adjustment must be made for errors in the results caused by small changes in the distance between the end of the fiber and reflecting surface 24.

Figure 8:
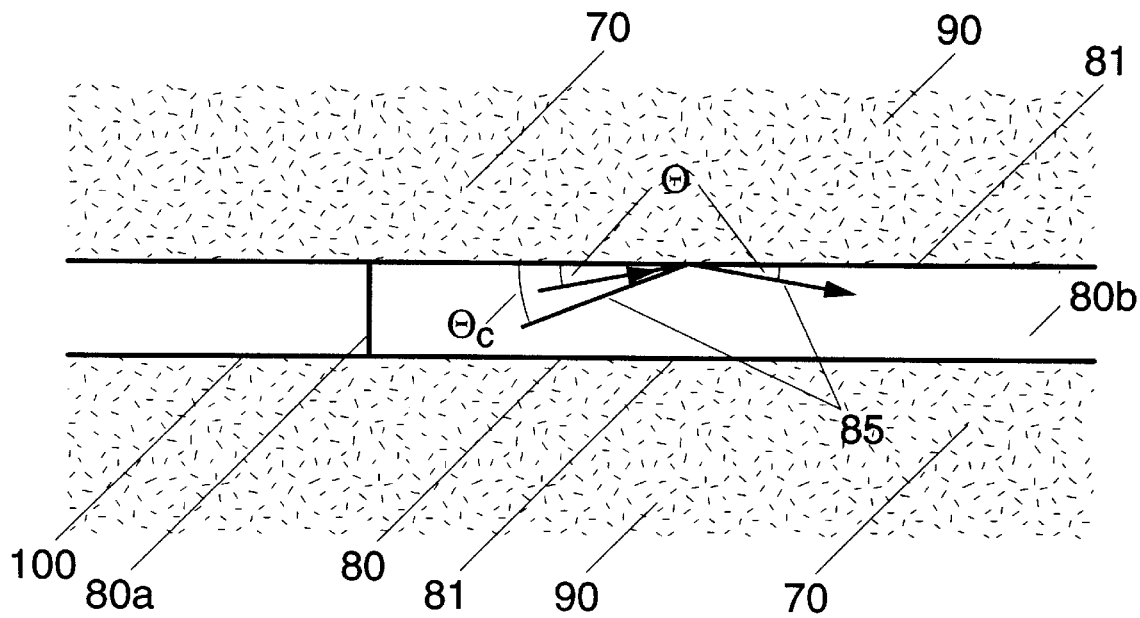
FIG. 8 is a schematic of another embodiment of this invention where the optical fiber is woven into the electrolyte of an absorbed-glass-mat battery.

In yet another embodiment, typical of an absorbed glass mat battery (a structural configuration also used for a lead-acid type battery), the absorptive electrolyte serves as the cladding of the optical fiber and introduces attenuated total internal reflection to what would otherwise be perfectly lossless, guided modes. FIG. 8 is a schematic of this embodiment of the present invention where the optical fiber is woven into the electrolyte of the battery, thereby forming part of the mat which holds the electrolyte by surface tension. As shown in FIG. 8, the electrolyte 70 of the battery acts as the lossy cladding of an otherwise unclad optical fiber 80. The single unclad optical fiber 80 is woven into the mat 90, here depicted as being similar to a sponge which contains the electrolyte 70. Instead of the reflecting surface 24 of FIG. 1, the reflecting surface in FIG. 8 is the structural interface 81 between the fiber 80 and the mat 90 in the configuration of FIG. 8. The ends 80*a* and 80*b* of fiber 80 may be connected to auxiliary fiber(s) 100 that act as lead fibers connecting the fiber 80 to a remotely-located light source (not shown) and detector (not shown).

With this configuration, the bulk absorption in the cladding causes some energy loss where total internal reflection would normally occur. This loss of energy is proportional to the bulk absorption coefficient, $\alpha$. Thus, as a light ray progresses down fiber 80 by bouncing off the core-cladding interface 81, it loses energy at each bounce; incident and reflected rays at the fiber-electrolyte boundary are shown as 85 in FIG. 8. Although the energy loss per bounce is small, the accumulated loss after a large number of bounces can be significant even for a modest length of fiber.

Equation 2 below provides the basis for the estimation of the length of fiber required to receive a good signal for the embodiment of FIG. 8. It is generally known that when a light ray travels in a lossless medium of a particular refractive index, the light impinges upon the boundary between it and a second, slightly absorbing, medium of lower refractive index. The light suffers the following approximate fractional loss of power upon reflection:

$$T = 4(\theta_c^2 - \theta^2)^{-1/2}(\theta/\theta_c^2)\, 5(\lambda\alpha/4\pi n), \qquad (2)$$

where T is fractional loss of power; $\theta_c$ is the critical angle for the two media; $\theta$ is the angle of incidence at the boundary between them; $\lambda$ is the optical wavelength; $\alpha$ is the bulk absorption coefficient of the lossy medium; and n is the real part of the refractive index of the lossy medium (A. W. Snyder and J. D. Love, *Optical Waveguide Theory*, Chapman and Hall, London, 1983, p.675). It should be noted that both P and $P_c$ are measured from the plane of the boundary, not the normal to it. According to Equation 2, the fractional power reflected back into the original medium is 1−T and the fraction of the original power remaining after N reflections is $(1-T)^N$.

Applying Equation 2 to a sensor fiber consisting of a glass core and the electrolyte cladding (i.e., the embodiment of FIG. 8) that is connected to an optical source via a conventional fiber having a numerical aperture of 0.3, and further assuming (1) that both cores have a refractive index of 1.46, (2) that the refractive index of the electrolyte varies from approximately 1.38 (in the visible) at full charge to approximately 1.35 at discharge, and (3) that the refractive index of the solution is 1.365, then under these conditions, the numerical aperture of the sensor fiber is greater than that of the conventional fiber (0.52 vs. 0.30). Therefore, for all rays in the sensor fiber that are short enough where mode mixing is negligible, $\theta$ is seen to be considerably less than $\theta_c$. The maximum value of $\theta$ is approximately 12° (0.21 radians) and the value of $\theta_c$ is approximately 21° (0.36 radians).

Returning to FIG. 5, at a wavelength of, for example, 1.45 micrometers, the absorbance is about 1 for the electrolytic solution at a pathlength of 1 mm. Therefore, $\alpha$ is approximately 2.3/mm. Using Equation 2, the fractional loss of power is about $4.2 \times 10^{-3}$. It follows that the number of reflections required to produce an absorbance of 1 through this mode of transmission is 547. Assuming a fiber diameter of 100 micrometers (0.004"), this number of bounces requires a length of about 26 cm (~10.4") for meridional rays. In the case of rays having $\theta$ equal to 0.1, the fractional loss of power is seen to be about $1.7 \times 10^{-3}$. Consequently, the corresponding number of bounces is 1357, and the resulting fiber length is computed to be about 65 cm (~26").

In another embodiment of the present invention, the sensor's structure is varied to project the light in a dominant direction with respect to the fiber. The term dominant, as used in connection with the sensor of the invention, refers to launching the light at an angle with respect to the optical fiber axis (launch meaning the initial direction that the light travels with respect to the fiber optic axis). In the configuration of the sensor using the unclad fiber, angle of launch at least partially controls the choice of length of fiber. Angle of launch is particularly a consideration when using the present invention with an absorbed glass mat battery. Using the embodiment shown in FIG. 8 to illustrate this concept, the optical fiber 80 is beveled, and light emitted from it is collimated, which steers the beam off-axis so that the rays are directed preferentially to a critical angle (i.e., $\theta$ will be closer to $\theta_c$, in general.). This allows the engagement of many otherwise tightly-bound rays in the absorption process and increases the dynamic range of the sensor.

In operation, the sensor of the present invention may exhibit a dependence on temperature or even multiple temperature dependencies for different absorption peaks, thus creating a temperature-induced error in the measurement. The peak with the highest concentration dependence to temperature dependence ratio, rather than the one with simply the highest concentration dependence, may then be the most desirable candidate for use in the sensor's measurement (even though the signal is somewhat less), because at that peak the temperature-induced error is the smallest.

Again using the lead-acid battery as an example, to the extent that the optical absorption depends on water concentration, the temperature-induced fractional error will be the same as the thermal expansion of the solution. Between 15° C. and 25° C., the average thermal expansion of a 1.22 gm/cc sulfuric acid solution is $3.28 \times 10^{-4}$/° C. Under the assumption that optical absorption depends on water concentration, the error incurred in heating the solution from 0° C. to 56° C. will be 1.83%. This error may be small enough to ignore; however, the optical absorption sensor of the present invention may include a temperature compensation feature to correct the error.

One option for temperature correction is that the sensor of the invention may include a conventional (electrical) means for determining the temperature, e.g., a thermocouple placed against the housing of the battery. The actual temperature and a previously measured temperature dependence of the absorption may be combined (e.g., by advance programming in the microprocessor) to correct the temperature-induced error, provided that the external temperature measurement is accurate enough for the particular application.

Alternatively, a correction involving a temperature measurement internal to the battery may be used; however, any internal temperature correction must be made optically to maintain the non-interfering character of the sensor. The sensor of the invention may include an optically-based temperature correction in which measurements are made at two different wavelengths, those wavelengths being chosen so that the absorption coefficients at the two wavelengths have the same (additive) temperature correction, and the difference in the absorption coefficients is therefore independent of temperature. If the absorption at the two wavelengths does not have the same temperature correction, and the absorption at the first wavelength is both concentration- and temperature-dependent, while the absorption at the second wavelength is temperature-dependent, but independent of sulfuric acid concentration throughout the relevant temperature range, then the absorption at the second wavelength acts as a temperature sensor for the "active" wavelength. For example, as seen in FIG. 3, the concentration-independent absorption at about 1.08 micrometers may be used as a temperature correction for the sensor of the invention.

Whether the temperature correction includes an external measurement or is completely internal, the microprocessor of the optical sensor is programmed to calculate the adjustment once the pertinent data are received.

Although the invention has been described in detail with particular reference to these preferred embodiments, the foregoing disclosure, description and drawings herein are only illustrative of particular embodiments of the invention and are not intended to be in any sense limiting. To those skilled in the art to which this invention relates, variations, modifications and different embodiments and applications of the invention will be obvious from the spirit and scope of the invention, as well as other objects, advantages and features of the invention. It is intended to cover in the appended claims all such modifications and equivalents. The scope of the invention is defined by, and the objects and advantages of the invention may be realized and attained by, the instrumentalities and combinations addressed in the appended claims. The entire disclosures of all references, applications, patents, and publications cited above, are hereby incorporated by reference.

What is claimed is:

1. A system for determining the state-of-charge of a battery having a conductor that changes in chemical composition with discharge, comprising:

a means for emitting light at a pre-determined wavelength and a pre-determined pathlength into the conductor, wherein said predetermined wavelength is chosen from a plot of the absorption coefficient of the conductor versus a plurality of wavelengths at a chosen limit of the chemical composition of the conductor and said pre-determined pathlength is chosen to correspond to said pre-determined wavelength and the transparency of the conductor;

a means for optically interrogating the conductor to obtain optical absorption at said pre-determined wavelength, the optical absorption varying with the changes in chemical composition in the conductor with discharge;

a means for detecting the varying optical absorption in the conductor, said detecting means being operably connected to said optically interrogating means;

a means for converting the detected optical absorption to state-of-charge information capable of being read by a user of the battery; and a means for displaying the state-of-charge information to the user of the battery.

2. The system of claim 1, wherein the battery is a lithium-ion battery.

3. The system of claim 1, wherein the battery is a lead-acid battery.

4. The system of claim 3, wherein said pre-determined wavelength is 1.45 $\mu$m and said pre-determined pathlength is 1 mm.

5. The system of claim 3, wherein said pre-determined wavelength is 0.97 $\mu$m and said pre-determined pathlength is 20 mm.

6. The system of claim 3, wherein said pre-determined wavelength is 1.20 $\mu$m and said pre-determined pathlength is 10 mm.

7. The system of claim 1, (a) wherein said optically interrogating means comprises:

a means for transmitting light from said light-emitting means through the conductor, thereby generating an optical signal that changes in optical power concurrently and proportionally with changes in the optical absorption in the conductor at said pre-determined wavelength, the changes, in optical absorption in the conductor occurring with battery discharge, a means for extracting the changing optical signal as output from the conductor, and a means for receiving the signal output from the conductor, said receiving means being operably connected to said detecting means, and for communicating said signal output to said detecting means; and (b) wherein said detecting means detects the optical power changes in the signal output.

8. The system of claim 7, wherein said optically interrogating means comprises a fiber optic means for transmitting the emitted light through the conductor and a fiber optic means for receiving the signal output from the conductor.

9. The system of claim 8, wherein said fiber optic transmitting means comprises at least one optical fiber and said fiber optic receiving means comprises a plurality of optical fibers.

10. The system of claim 8, wherein:

said fiber optic transmitting means and said fiber optic receiving means comprise a fiber optic bundle, said bundle comprising at least one central transmitting fiber for introducing emitted light into the conductor, at least six receiving fibers surrounding said central transmitting fiber for receiving the signal output from the conductor, a first end operably connected to said detecting means, and a second end, and said second end having a polished face for preventing light from scattering randomly at an interface between said fiber optic means and the conductor.

11. The system of claim 8, wherein said fiber optic transmitting means and said fiber optic receiving means comprise a single unclad optical fiber, the conductor is contained by a material that forms a cladding surrounding said optical fiber, and said fiber is woven into said cladding material.

12. The system of claim 11, wherein the battery is an absorbed-glass-mat battery.

13. The system of claim 8, wherein said fiber optic transmitting means and said fiber optic receiving means comprise a single optical fiber having a means for splitting light emitted into the conductor from said light-emitting means into transmitted light and received light.

14. The system of claim 8, wherein said fiber optic transmitting means and said fiber optic receiving means comprise at least one optical fiber having an axis, an input end and an output end, and wherein said input end of said optical fiber is beveled and light from said emitting means is emitted into the conductor at a predetermined angle to the axis of said optical fiber.

15. The system of claim 7, wherein said extracting means comprises a reflecting means.

16. The system of claim 8, wherein said reflecting means comprises a reflecting surface, said reflecting surface shaped to maximize the reflected signal output returned to said receiving means.

17. The system of claim 7, wherein said extracting means comprises an interface between said optically interrogating means and the conductor, and the length of said optically interrogating means is chosen to maximize the signal output returned to said receiving means.

18. The system of claim 7, wherein said detecting means comprises a photodetector that receives the signal output from said receiving means and converts detected power changes therein to an electric current, said current changing in direct proportion to the optical power changes in the transmitted light.

19. The system of claim 1, wherein said converting means comprises a means for converting detected optical adsorption into a voltage signal, and a means for converting the voltage signal to state-of-charge information capable of being communicated to the user of the battery.

20. The system of claim 1, wherein said converting means comprises a means for mathematically adjusting the optical absorption information to provide directly proportional state-of-charge information.

21. The system of claim 1, further comprising a means for compensating for temperature-induced error in optical absorption obtained by said optically interrogating means.

22. The system of claim 21, wherein said means for compensating for temperature-induced error comprises a means for pre-determining a temperature dependence of absorption in the conductor, an electrical means for determining exact temperature of the conductor, and a means for combining the pre-determined temperature dependence with the exact temperature, and said means for converting further comprises a means for calculating an adjustment to correct for temperature induced errors in the detected absorption information at the chosen wavelength.

23. The system of claim 1, wherein the conductor comprises at least one pair of electrodes, one of said pair being the cathode and the other being the anode, and said optically interrogating means comprises a means for transmitting light through the anode, a means for extracting the transmitted light out of the anode, the transmitted light changing in optical power corresponding to variation in optical absorption in the conductor during transmission, a means for receiving the changing transmitted light and a means for communicating the optical power changes in the transmitted light to said detector.

24. The system of claim 1, wherein said means for optically interrogating the conductor to obtain optical absorption information comprises:

an absorption cell in operable association with said conductor, said cell having a housing comprising a first end, a second end and an interior reflecting surface located at said second end of said housing, said reflecting surface shaped to maximize the reflected signal output returned to said receiving means, a fiber optic means for transmitting light into the conductor and for receiving reflected light from the conductor, said fiber optic means having a first end and a second end, said first end of said fiber optic means being operably attached to said light-emitting means and to said detecting means, and said second end of said fiber optic means being operably attached to said cell at at least one opening at said first end of said housing, whereby said fiber optic means transmits light emitted by said light emitting means through the conductor, said light changing in optical power corresponding to changing optical absorption during transmission through the conductor, and said changing transmitted light is reflected by said interior reflecting surface back to said fiber optic means, thereby providing absorption information communicable to said detecting means.

25. The system of claim 24, wherein the conductor is an electrolyte, and said cell is inserted in the electrolyte and comprises at least two openings whereby at least a portion of the conductor flows through said cell.

26. The system of claim 25, wherein said cell comprises a third opening whereby emitted light from said light emitting means is transmitted into and out of the conductor.

27. The system of claim 26, wherein said third opening comprises a window.

28. A method for determining the state-of-charge of a battery having a conductor that changes in chemical composition with discharge, comprising the steps of:

choosing a wavelength from a plot of the absorption coefficient of the conductor versus a plurality of wavelengths;

choosing a pathlength to correspond to said pre-determined wavelength and the transparency of the conductor;

emitting light at the pre-determined wavelength and the pre-determined pathlength into the conductor;

optically interrogating the conductor to obtain changes in absorption in the conductor during discharge of the battery, the changes in absorption being manifested as changes in optical power in the light;

detecting the optical power changes;

converting the optical power changes to state-of-charge information communicable to a user of the battery; and displaying the state-of-charge information to the user of the battery.

29. The method of claim 28, wherein the step of optically interrogating the conductor comprises the steps of:

(a) transmitting light through the conductor, whereby the optical power of the transmitted light changes corresponding to changes in optical absorption characteristics of the conductor proportional to changes in state-of-charge of the battery, and (b) extracting the optical power changes out of the conductor as a changing electrical signal output.

30. The method of claim 28, wherein the battery is a lead-acid battery, the conductor is an aqueous electrolytic solution of sulfuric acid, and the step of optically interrogating the conductor to obtain changes in optical absorption comprises the step of measuring the decline in optical attenuation in the conductor at at least one characteristic absorption peak of pure water.

31. The method of claim 28, further comprising the step of compensating for errors in state-of-charge information resulting from temperature dependence of optical absorption at the predetermined wavelength.

32. The method of claim 31, wherein said temperature-compensating step comprises the steps of pre-determining a temperature dependence of absorption in the conductor, electrically measuring the actual temperature of the battery, mathematically combining said actual temperature with the pre-determined temperature, and said converting step further comprises the step of calculating an adjustment to correct for temperatureinduced variation in absorption at the pre-determined wavelength.

33. The method of claim 31, wherein said temperature-compensating step comprises the steps of obtaining optical absorption at at least two pre-determined wavelengths and said converting step further comprises the step of calculating an adjustment to correct for errors in the detected optical absorption at said at least two pre-determined wavelengths.

34. The method of claim 33, wherein said at least two pre-determined wavelengths are chosen to provide absorption coefficients having the same additive temperature correction, and said calculating step further comprises the step of subtracting optical signals obtained at said two pre-determined wavelengths, thereby canceling the temperature dependence and providing a temperature-independent optical signal.

35. The method of claim 33, wherein said at least two pre-determined wavelengths are chosen to provide absorption coefficients with differing temperature correction, whereby at least one of said at least two wavelengths is temperature-dependent but independent of the concentration of the conductor, and the other of said at least two wavelengths is temperature-dependent and concentration-dependent, and comprising the step of using said at least one temperature-dependent, concentration-independent wavelength as a temperature correction.

36. The method of claim 35, wherein said at least one temperature-dependent, concentration-independent wavlength is 1.08 $\mu$m.

37. The system of claim 28, wherein the step of converting the optical absorption information to state-of-charge information further comprises the steps of:

converting the optical power changes into a voltage signal, converting the voltage signal to a state-of-charge information capable of being communicated to the user of the battery, mathematically adjusting the voltage signal to provide directly proportional state-of-charge information.

* * * * *